United States Patent [19]
Jacob

[11] Patent Number: 6,162,604
[45] Date of Patent: Dec. 19, 2000

[54] METHODS FOR DETERMINING GENETIC PREDISPOSITION TO AUTOIMMUNE DISEASES BY GENOTYPING APOPTOTIC GENES

[76] Inventor: Chaim O. Jacob, 2110 Beverwil Dr., Los Angeles, Calif. 90034

[21] Appl. No.: 09/283,040

[22] Filed: Apr. 1, 1999

[51] Int. Cl.[7] .............................. C12Q 1/68; C12P 19/34; C07H 21/04
[52] U.S. Cl. .......................... 435/6; 435/91.2; 536/24.31; 536/24.33
[58] Field of Search .................... 435/6, 810; 536/24.31, 536/24.33

[56] References Cited

PUBLICATIONS

Tsujimoto et al., "DNA rearrangements in human follicular lymphoma can involve the 5' or 3' region of the bcl–2 gene", Proceedings of the National Academy of Sciences, USA, vol. 84, pp. 1329–1331, Mar. 1987.

Platzer et al., "Up–regulation of monocytic IL–10 by tumor necrosis factor–alpha and cAMP elevating drugs", International Immunology, vol. 7 (4), pp. 517–523, Dec. 1994.

Alderson et al., "Fas ligand Mediates Activation–induced cell death in human T lymphocytes", Journal of Esperimental Medicine, vol. 181, pp. 71–77, Jan. 1995.

Harley et al., "Lupus and Interleukin 10", Journal of Rheumatology, vol. 24 (12), pp. 2273–2275, 1997.

Aringer et al., "High levels of bcl–2 protein in circulating T lymphocytes, but not B lymphocytes of patients with systemic lupus erythematosus", Arthritis and Rheumatism, vol. 37 (10), pp. 1423–1430, Oct. 1994.

Donner et al., "CTLA4 alanine–17 confers genetic susceptibility to Graves' disease and to Type 1 Diabetes Mellitus", Journal of clinical endiocrinology and metabolism, vol. 82 (1), pp. 143–146, 1997.

Huang et al., "Identification and characterization of polymorphism in the promoter region of the human Apo–1/Fas (CD95) gene", Molecular Immunolgy, vol. 34 (8–9), pp. 577–582, 1997.

Eskdale, et al., Association between polymorphisms at the human IL–10 locus and systemic lupus erythematosus, *Tissue Antigens* 49:635–639 (1997).

Polymeropoulos, et al., Tetranucleotide repeat polymorphism at the human c–fes/fps proto–oncogene (FES), *Nucleic Acids Research* 19(14):4018 (1991).

Tan et al., The 1982 Revised Criteria For The Classification of Systemic Lupus Erythematosus, *Arthritis and Rheumatism* 25(11):1271–1277 (1982).

Turner, et al., An Investigation of Polymorphism in the Interleukin–10 Gene Promoter, *European Journal of Immunogenetics* 24:1–8 (1997).

*Primary Examiner*—Jeffrey Fredman
*Assistant Examiner*—Arun Chakrabarti
*Attorney, Agent, or Firm*—Knobbe Martens Olson & Bear, LLP

[57] ABSTRACT

Genetic markers associated with programmed cell death were characterized and their extent of polymorphism in normal populations was determined allowing for a method for determining genetic predisposition to SLE and other autoimmune diseases by genotyping. The allelic distribution of these gene markers in a large Mexican American SLE cohort and ethnically matched controls was determined. The results were that bcl-2, Fas-L, and IL-10 loci showed significantly different allelic distribution in SLE patients compared with controls, indicating an association between these gens and SLE. The method allows for determining the presence of these alleles. Alone, the presence of each of these alleles is associated with a moderate increase in SLE risk, while the occurrence of these alles together increases the odds of developing SLE by more than 40-fold.

10 Claims, No Drawings

METHODS FOR DETERMINING GENETIC PREDISPOSITION TO AUTOIMMUNE DISEASES BY GENOTYPING APOPTOTIC GENES

FIELD OF THE INVENTION

This invention relates generally to methods for determining predisposition to systemic lupus erythematosus (SLE) and other autoimmune diseases by genotyping IL-10, bcl-2, FAS ligand (FAS-L) and other apoptotic genes. More specifically, the bcl-2, Fas-L, and IL-10 loci showed significantly different allelic distribution in SLE patients compared with controls, indicating an association between these genes and SLE. Additionally, further analysis revealed a synergistic effect between susceptibility alleles of the bcl-2 and IL-10 genes in determining disease susceptibility.

BACKGROUND OF THE INVENTION

Systemic lupus erythematosus (SLE) is considered to be the prototype of human autoimmune diseases. It is a disorder of generalized autoimmunity characterized by multisystem organ involvement, polyclonal B cell activation, and the production of autoantibodies against nuclear, cytoplasmic, and cell surface antigens. Autoreactive B and T lymphocytes can be found in healthy individuals as well, but their numbers are tightly regulated by a process of programmed cell death (apoptosis), which is crucial in the establishment of self-tolerance. Tolerance to self antigens can fail and can result in autoimmunity if there is a defect in the process of elimination of these cells.

SLE, as well as most other autoimmune diseases is difficult to diagnose. A strict definition of SLE patients included 4 or more of the 11 ACR revised criteria for SLE, eliminating LE cells but adding anticardiolipin antibodies and lupus anticoagulant as criteria (Tan, et al. Arthritis Rheum. 1982;25:1271–7). Often, a patient that is going to develop SLE will be kept off of treatment because they only show two or three of the criteria. One of the major tests, the ANA test (anti-nuclear antibodies), tests for the presence of these antibodies. However, 15–20% of those individuals with a positive ANA will never develop disease. The inadequacy of definitive tests for the diagnosis of autoimmune diseases is a recurrent theme. For this reason, treatment is often not started until disease is too far along and irreversible damage has occurred. Therefore development of a test for the diagnosis and susceptibility to autoimmune diseases could have a profound effect on the outcome of the disease and the patient's quality of life.

Several lines of evidence suggest that dysfunctional programmed cell death (apoptosis) might be involved in the pathogenesis of SLE and other autoimmune diseases. It has been postulated that in SLE, dysfunction of apoptosis could result in the inappropriate longevity of autoreactive B lymphocytes, allowing autoantibody levels to reach pathogenic thresholds and breakdown of self tolerance. Defective apoptosis of autoreactive lymphocytes is an attractive mechanism contributing to SLE, primarily because defects in either the apoptosis-promoting Fas gene or its ligand Fas-L (CD95L) accelerates autoimmunity in mouse strains (MRL-lpr/lpr and C3H-gld/gld, respectively) that exhibit SLE-like diseases. Furthermore, studies reveal links between autoimmunity and several other gene products involved in apoptosis. The bcl-2 gene enhances lymphocyte survival by inhibiting or delaying apoptosis. Transgenic mice overexpressing bcl-2 in their B cells show polyclonal B cell expansion and extended survival in vitro. After a few months, these mice developed an autoimmune syndrome resembling SLE.

Interleukin-10 (IL-10) is a pleiotropic cytokine that regulates many immune and inflammatory responses. Among other activities, this cytokine increases the survival of activated lymphocytes. Furthermore, administration of recombinant IL-10 to lupusprone (New Zealand black×New Zealand white)$F_1$ ([NZB×NZW]$F_1$) mice accelerates the development of autoimmunity. CTLA-4 is an additional gene involved in apoptosis that has been suggested to be associated with autoimmune disease development. CTLA4 can mediate antigen-specific apoptosis and appears to be part of a distinct signaling pathway capable of clonally deleting previously activated human T lymphocytes. CTLA-4 also warrants further study because it may be a candidate gene in more than one autoimmune disease. CTLA-4 was reported to be associated with 2 autoimmune diseases, Grave's disease and insulin-dependent diabetes mellitus.

In a recent publication, Eskdale et al (Tissue Antigens 1997;49:635–9) have shown an association between an IL-10 microsatellite polymorphism and SLE in a Caucasian population. In this study a group of 56 Caucasian SLE patients from Great Britain were compared with 102 ethnically matched controls. However, because of the moderate sample size, the results were considered only as a framework for further study.

SUMMARY OF THE INVENTION

One object of the present invention is a method for determining predisposition to an autoimmune disease by obtaining a patient sample, amplifying at least two apoptotic loci, and determining whether the disease-specific allele is present.

A further embodiment includes identifying the disease-specific alleles by comparing the most abundant allele found in patients with disease to normal individuals. Preferably the apoptotic gene loci are selected from the group consisting of IL-10, bcl-2, Fas-L, and CTLA-4. Preferably, the IL-10 disease-associated allele is PCR amplified with the primers comprising SEQ ID NO:1 and SEQ ID NO:2, the bcl-2 disease-associated allele is PCR amplified with the primers comprising SEQ ID NO:3 and SEQ ID NO:4, the Fas-L disease-associated allele is PCR amplified with the primers comprising SEQ ID NO:5 and SEQ ID NO:6, and the CTLA-4 disease-associated allele is PCR amplified with the primers comprising SEQ ID NO:7 and SEQ ID NO:8. In a further preferred embodiment, the disease-associated allele is identified by size or sequence. Preferably, the disease is selected from the group consisting of; systemic lupus erythematosis, thyroid autoimmunity syndromes, insulin dependent diabetes mellitus, inflammatory bowel disease, rheumatoid arthritis and other arthritidies.

A further object of the invention is a kit for determining predisposition to an autoimmune disease comprising the method of claim 1.

A further object of the invention is a method for producing a diagnostic test for predispostion to an autoimmune disease which involves obtaining a patient sample, PCR amplifying at least two apoptotic loci, and identifying the disease-specific alleles by comparison to normal individuals, finally determining whether the disease-specific allele is present in a test patient's sample.

DETAILED DESCRIPTION OF THE INVENTION

Because bcl-2, Fas-L, CTLA-4, and IL-10 participate in apoptosis, and because of the evidence suggesting that these genes may be involved in the pathogenesis of SLE, we tested whether there is an association between these genes and SLE in humans.

The method of the present invention comprises a technique for determining the presence of disease-associated alleles of apoptotic genes and analyzing whether they show predisposition to autoimmune diseases.

Further features and advantages will become apparent to those of skill in the art in view of the Detailed Description of the Invention which follows, when considered together with the attached claims.

Although other materials and methods can be used in the practice or testing of the present invention, a method is now described. Examples 1–3 show how a method for determining predisposition to an autoimmune disease can be developed.

EXAMPLE 1

Characteristics of the Study Population

Patients in this study were from the University of Southern California (USC) School of Medicine clinics who were confirmed to have met the American College of Rheumatology (ACR) criteria for SLE. A strict definition of SLE patients included 4 or more of the 11 ACR revised criteria for SLE, eliminating LE cells but adding anticardiolipin antibodies and lupus anticoagulant as criteria (Tan, et al. Arthritis Rheum. 1982:25:1271–7).

We used semistructured personal or telephone interviews to obtain a complete family history of each SLE patient and control subject. Through these interviews, data were collected describing a fixed family structure (proband's grandparents, parents, siblings, and offspring, as well as siblings and offspring of both of the proband's parents). Information regarding the birthplace of the probands, their parents, and their grandparents was also obtained. Whenever possible, we obtained family history information about the probands from an additional source (usually, a parent of the subject).

For the purpose of this study, Mexican Americans were defined as individuals born in Mexico or the US whose grandparents from both the mother's and the father's side were born in Mexico. Controls were defined as Mexican American subjects who did not have SLE or any other autoimmune disease and whose family lacked any autoimmune disease history. The study protocol was approved by the Institutional Review Board of the USC School of Medicine.

EXAMPLE 2

Genotypic Analysis of IL-10, bcl-2, Fas-L, and CTLA-4

Blood samples were collected from all participants, and genomic DNA was extracted from the peripheral blood mononuclear cells by standard procedures. To obtain genotypes of the IL-10, bcl-2, and Fas-L, short tandem repeat sequences (microsatellites) within the noncoding regions of these genes were identified and used as intragenic markers. The Fas-L $(TG)_n$ tandem repeat was identified in the 3'-untranslated region of the gene, ~600 basepairs after the stop codon, while the IL-10 $(CA)_n$ microsatellite is located ≠1 kb 5' to the ATG codon. The CTLA-4 dinucleotide repeat begins at bp 642 of exon 3 of the human CTLA-4 gene (Polymeropoulos, et al. Nucleic Acids Res 1991:19:4018), and the bcl-2 $(AC)_n$ microsatellite is located 570 bp 5' to the ATG codon. (The IL-10, bcl-2, and Fas-L gene sequences can be found using Genomic Data Base accession numbers X78437, X51898, and GenBank number U08137, respectively).

To amplify or image these loci, PCR was performed as follows: unique oligonucleotide sequences flanking each microsatellite were designed as primers, one of which was labeled with a fluorescent dye and used in the polymerase chain reaction (PCR). The oligonucleotides flanking the IL-10 $(CA)_n$ repeat were the 5' primer 5'-GCA ACA CTC CTC GTC GCA AC-3' (SEQ ID NO:1) and the 3' primer, tagged with the fluorescent dye 6FAM, 5'-CCT CCC AAA GAA GCC TTA GTA G-3' (SEQ ID NO:2). The oligonucleotides flanking the bcl-2 (AC), repeat were the 5' primer, tagged with the fluorescent dye TET, 5'-CGT GTA CAC ACT CTC ATA CAC GGC T-3' (SEQ ID NO:3) and the 3' primer 5'-GGG AGG GTG CGC CAT GAA AA-3' (SEQ ID NO:4). The oligonucleotides flanking the Fas-L $(TG)_n$ repeat were the 5' primer, tagged with the fluorescent dye 6FAM, 5'-CA CTT CT AAA TGC ATA TCC TGA GCC-3' (SEQ ID NO:5) and the 3' primer 5'-TGT CAG GAA GCA TTC AAA ATC TTG ACC A-3' (SEQ ID NO:6).

For CTLA-4, we used an $(AT)_n$ microsatellite marker previously described (Polymeropoulos, et al. Nucleic Acids Res 1991:19:4018). The oligonucleotides flanking the CTLA-4 $(AT)_n$ repeat were the 5' primer, tagged with the fluorescent dye TET, 5'-GCC AGT GAT GCT AAA GGT TG-3' (SEQ ID NO:7) and the 3' primer 5'AAC ATA CGT GGC TCT ATG CA-3' (SEQ ID NO:8).

PCR amplification was carried out using 40 ng of genomic DNA. The reaction conditions consisted of 0.5 μM of each primer (labeled and unlabeled), 10 mM Tris HCl, pH 8.8, 50 mM KCl, 1.5 mM $MgCl_2$, 50 μM of each dNTP, and 0.2 units of Taq polymerase. For IL-10, the samples were processed through 30 cycles of 30 seconds at 94° C., 30 seconds at 57° C., and 30 seconds at 72° C. For CTLA-4 the conditions were 30 seconds at 94° C., 120 seconds at 55° C., and 30 seconds at 72° C.

A "touchdown" PCR assay for Fas-L and bcl-2 polymorphism was performed to circumvent spurious priming during amplification. The initial annealing temperature was 66° C.; subsequent annealing temperatures were decreased by 1° C. every cycle to a "touchdown" annealing temperature of 55° C., at which 30 cycles of 1 minute at 94° C., 1 minute at 55° C., and 1 minute at 72° C. were performed.

Aliquots of the PCR product were electrophoresed on a 377 Prism ABI sequencer (Applied Biosystems, Foster City, Calif.), and the fluorescent signal was recorded and analyzed by the Genescan software (Applied Biosystems). Different fluorescent dyes were plotted separately, and the sizes of the fluorescent peaks were estimated in basepairs by reference to the in-lane size standard Tamra 500 (Applied Biosystems). Microsatellite alleles were classified automatically according to their size using the Genotyper software (Applied Biosystems). For quality control to ensure reproducibility of allele assignments between gels, 1 lane in each gel was loaded with a sample that had previously been genotyped. Each lane of the sequencing gel was loaded with the internal size marker labeled with Tamra 500. In addition to the automated allele calling, we performed manual surveillance of every genotype.

Although Example 2 makes use of PCR amplification to determine sequence length polymorphisms, one of skill in the art can readily identify other methods for the purpose of identifying disease-specific alleles. Single point mutations can also be readily identified using a number of techniques well known to those having ordinary skill in the art. Examples of such methods to identify small allelic differences include FISH (Fluoescence In Situ Hybridization, RFLP (Restriction fragment length polymorphism), TGGE (temperature gradient gel electrophoresis) and SSCP (single-strand conformation polymorphism), each of which can be used to identify differences in DNA or RNA. Pure hybridization methods, such as Southern blotting or DNA chip technology, can also be used. Alternatively differences in the protein product could be imaged or identified using such techniques as Western blotting, ELISA, or even enzymatic assays.

EXAMPLE 3

Statistical Analysis

Associations between loci and the presence of SLE were tested by fitting a logistic regression model to the data. Genotypes at each locus were coded assuming a multiplicative model for allelic effects. Under this model, the odds ratio for a person with alleles $a_i$ and $a_j$ is given by $e^{b_i} e^{b_j}$, where $b_i$ and $b_j$ are regression coefficients corresponding to $a_i$ and $a_j$, respectively. For each locus, alleles that occurred in <3 subjects were eliminated from the analysis. The likelihood ratio test was used as a global test of association between each locus and the presence of SLE.

Pairwise interactions between IL-10, Fas-L, and bcl-2 alleles were modeled using a departure from a multiplicative model for the corresponding joint locus effects. At each locus, a genotype for each subject was coded based on the presence or absence of at least 1 copy of the corresponding high-risk allele. Using a logistic regression model, the likelihood ratio test was used to determine whether each interaction significantly improved the model fit compared with a model including only the main effects on the 2 component loci.

A significance level of 0.05 was used in all global testing. A bonferroni adjustment was used in determining the significance of individual alleles. P values are reported for all tests so that the reader may independently assess statistical significance

EXAMPLE 4

Association of SLE with Apoptotic Markers

Highly polymorphic short tandem repeat sequences (microsatellites) within the noncoding regions of the Fas-L, bcl-2, and IL-10 genes were identified and characterized as part of the present study, and were used as markers (see EXAMPLE 1). The polymorphism information content scores were 0.72 for IL-10, 0.47 for bcl-2, 0.59 for Fas-L, and 0.83 for CTLA-4.

The allelic distribution of these microsatellites was determined in several distinct ethnic populations, including Caucasian Americans, African Americans, Chinese Americans, and Mexican Americans, and showed a significant variation among these ethnic groups. For example, Table 1 illustrates significant variation in bcl-2 allele frequencies among normal individuals belonging to 4 major ethnicities in the US. The global likelihood ratio, testing for differences in allelic distribution at bcl-2 among the 4 American populations, was $\chi^2=149.7$ (degrees of freedom [df]=18, P=0.001). Similar ethnic variation in marker allele frequencies was found in the other genes tested in this study. The allele frequencies observed in control populations conform to Hardy-Weinberg expectations.

TABLE 1

Allele distribution of bcl-2 microsatellite in various American populations*

| Allele (bp) | Frequency | | | |
|---|---|---|---|---|
| | CA (2n = 160) | AA (2n = 172) | MA (2n = 440) | ChA (2n = 100) |
| 187 | — | — | 0.002 | — |
| 191 | 0.063 | 0.169 | 0.177 | 0.260 |
| 193 | 0.025 | 0.081 | 0.048 | 0.030 |
| 195 | 0.831 | 0.430 | 0.700 | 0.470 |
| 197 | 0.025 | 0.047 | 0.029 | 0.120 |
| 199 | 0.006 | 0.041 | 0.009 | — |
| 201 | 0.031 | 0.180 | 0.029 | 0.120 |
| 203 | 0.019 | 0.047 | — | — |
| 207 | — | 0.005 | — | — |

*2n = number of chromosomes scored to determine allele frequencies; CA = Caucasian Americans; AA - African Americans; MA = Mexican Americans; ChA = Chinese Americans; bp = basepairs.

Since SLE itself occurs at a higher frequency in certain ethnic populations than in others, an association between the disease and a gene marker might occur as a statistical artifact in the mixed population. To minimize this potential problem of population stratification, we decided to focus the study on one ethnic population in detail. We focused on Mexican Americans since they comprise the majority of SLE patients in our center. The data presented below were obtained from 158 Mexican American SLE patients and 223 ethnically matched control subjects. Selected clinical characteristics of the SLE patients in the study are shown in Table 2. Both cohorts (SLE patients and control subjects) were not significantly different in age and sex distribution.

TABLE 2

Selected clinical characteristics of the study population*

| Characteristic | SLE patients (n = 158) | Control subjects (n = 223) |
|---|---|---|
| Age, mean ± SD years | 34.2 ± 11.6 | 35.4 ± 12.7 |
| Female, % | 90.5 | 86 |
| ANA positive, % | 100 | — |
| Anti-dsDNA positive, % | 61 | — |
| Renal involvement, % | 35 | — |
| CNS involvement, % | 9 | — |

*SLE = systemic lupus erythematosus; ANA = antinuclear antibodies; anti-dsDNA = anti-double-stranded DNA antibodies; CNS = central nervous system.

The allelic distributions of microsatellite markers of the bcl-2, IL-10, and Fas-L genes in SLE cases and in ethnically matched controls are summarized in Table 3. Associations between these loci and the presence of SLE were tested by fitting a logistic regression model to the data (see EXAMPLE 1).

Bcl-2 We identified 9 distinct alleles of the bcl-2 gene; the most frequent allele in the controls was 195-bp long (Bcl-$2_{195}$). The global likelihood ratio statistic, which tests for a difference in allelic distribution at bcl-2 between cases and controls, was $X^2=34.95$ (df=5, P=0.0001), indicating a definite association between the bcl-2 gene and SLE IL-10 Regarding the IL-10 gene, 10 distinct alleles were found in Mexican Americans. The most common allele in the control population was 125-bp long (IL-$10_{125}$). The test of association of this gene with SLE gave $\chi^2=33.20$ (df=8, P=0.0001), indicating an association.

Fas-L The Fas-L intragenic marker showed 7 distinct alleles; allele 241 was the most common in the control population. The global likelihood ratio test statistic for Fas-L was $\chi^2=23.99$ (df=6, P=0.0005), suggesting an association between Fas-L and SLE as well.

TABLE 3

Allele distribution of the intragenic markers of IL-10, bcl-2, and Fas-L in Mexican American SLE patients and normal controls*

| IL-10 allele frequency | | bcl-2 allele frequency | | | Fas-L allele frequency | | |
|---|---|---|---|---|---|---|---|
| Allele (bp) | Cases (2n = 316) | Controls (2n = 440) | Allele (bp) | Cases (2n = 312) | Controls (2n = 440) | Allele (bp) | Cases (2n - 298) | Controls (2n = 402) |

| Allele (bp) | Cases (2n = 316) | Controls (2n = 440) | Allele (bp) | Cases (2n = 312) | Controls (2n = 440) | Allele (bp) | Cases (2n - 298) | Controls (2n = 402) |
|---|---|---|---|---|---|---|---|---|
| 121 | 0.003 | 0.009 | 187 | — | 0.002 | 233 | 0.013 | 0.003 |
| 123 | 0.025 | 0.050 | 189 | 0.006 | — | 235 | 0.013 | 0.008 |
| 125 | 0.363 | 0.493 | 191 | 0.187 | 0.177 | 237 | 0.024 | 0.003 |
| 127 | 0.199 | 0.081 | 193 | 0.135 | 0.048 | 239 | 0.289 | 0.143 |
| 129 | 0.107 | 0.066 | 195 | 0.548 | 0.700 | 241 | 0.527 | 0.640 |
| 131 | 0.067 | 0.064 | 197 | 0.042 | 0.029 | 243 | 0.128 | 0.179 |
| 133 | 0.136 | 0.127 | 199 | 0.013 | 0.009 | 245 | 0.007 | 0.022 |
| 135 | 0.073 | 0.098 | 201 | 0.048 | 0.029 | | | |
| 137 | 0.022 | 0.006 | 203 | 0.026 | — | | | |
| 139 | — | 0.004 | | | | | | |

*2n = number of chromosomes scored to determine allele frequencies.
SLE = systemic lupus erythematosus.

CTLA-4 The CTLA-4 marker, however, showed no association with SLE. As shown in Table 4, the CTLA-4 marker had 19 distinct alleles in the Mexican American population. The likelihood ratio test result between cases and controls was $\chi^2=19.5$ (df=13, P=0.1074). (Five alleles of the CTLA-4 occurred so rarely in the data set that accurate estimates of their odds ratios could not be calculated. These alleles were left out of the analysis.)

To further investigate the significant associations, we performed additional analyses to determine which allele(s) of bcl-2, Fas-L, and IL-10 were associated with SLE. Table 5 summarizes the odds ratio (OR) and 95% confidence intervals (95% CI) for the effect of each allele relative to a baseline allele. The Bcl-$2_{193}$ and Bcl-$2_{201}$ alleles were associated with increased odds of developing SLE (OR 5.61, P=0.0001 and OR 3.15, P=0.006 per allele copy, respectively, compared with Bcl-$2_{195}$).

With regard to IL-10, only the IL-$10_{127}$ was associated with increased odds of developing SLE (OR 2.81 per allele copy, as compared with IL-$10_{125}$, P=0.0001). The Fas-$L_{239}$ allele was associated with increased odds of developing SLE (OR 1.69 per allele copy), as compared with the Fas-$L_{241}$ allele (P=0.001). As expected, the CTLA-4 gene showed no specific allele association with SLE (Table 5).

EXAMPLE 5

Synergistic Association of Il-10 and Bcl-2 Alleles

We next explored the possibility that synergistic effects between these loci may increase the risk of developing SLE. To this end, a departure from a multiplicative model for corresponding allelic effects was tested. To minimize the number of tests, we focused on single high-risk allele at each locus: allele 193 at bcl-2, allele 127 at IL-10, and allele 239 at Fas-L (see Table 5). The interaction tests are summarized in Table 6. We found no significant interaction between IL-10 and Fas-L, or between Fas-L and bcl-2. However, surprisingly there was significant interaction between the Il-$10_{127}$ allele and the Bcl-$2_{193}$ allele (P=0.004). Of 23 subjects that carried both the Bcl-$2_{193}$ and IL-$10_{127}$ alleles, 22 had SLE. While a person carrying either the IL-$10_{127}$ or the Bcl-$2_{193}$ allele only had an OR of ~2, a person carrying both the IL-$10_{127}$ and the Bcl-$2_{193}$ susceptibility alleles together had an OR of 40.71 (Table 7).

TABLE 4

Allele distribution of CTLA-4 in Mexican American SLE patients and normal controls.

| Allele (bp) | Cases (2n = 250) | Controls (2n = 446) |
|---|---|---|
| 88 | 0.564 | 0.581 |
| 94 | 0.004 | 0.006 |
| 96 | — | 0.006 |
| 102 | 0.012 | 0.004 |
| 104 | 0.076 | 0.058 |
| 106 | 0.188 | 0.222 |
| 108 | 0.036 | 0.027 |
| 110 | 0.036 | 0.009 |
| 112 | 0.008 | 0.004 |
| 114 | 0.008 | 0.006 |
| 116 | — | 0.004 |
| 118 | 0.012 | 0.070 |
| 120 | 0.016 | 0.002 |
| 122 | 0.008 | 0.004 |
| 124 | 0.016 | 0.012 |
| 126 | 0.008 | 0.011 |
| 128 | 0.004 | 0.006 |
| 130 | 0.004 | 0.020 |
| 132 | — | 0.006 |

*2n = number of chromosomes scored to determine allele frequencies.
SLE = systemic lupus erythematosus.

TABLE 5

Association between SLE and specific alleles of bcl-2, IL-10, and Fas-L, but not CTLA-4*

| | Allele | OR† | 95% CI | |
|---|---|---|---|---|
| bcl-2 | Baseline (195) | 1.00 | — | — |
| | 191 | 1.59 | 1.06, 2.37 | 0.024 |
| | 193 | 5.61 | 2.99, 10.53 | 0.0001‡ |
| | 197 | 1.75 | 0.72, 4.23 | 0.215 |
| | 199 | 1.42 | 0.39, 5.24 | 0.596 |
| | 201 | 3.15 | 1.38, 7.17 | 0.006‡ |
| IL-10 | Baseline (125) | 1.00 | — | — |
| | 121 | 0.43 | 0.04, 4.02 | 0.455 |
| | 123 | 0.63 | 0.27, 1.50 | 0.296 |
| | 127 | 2.81 | 1.78, 4.44 | 0.0001‡ |
| | 129 | 1.96 | 1.14, 3.38 | 0.015 |
| | 131 | 1.28 | 0.71, 2.29 | 0.416 |
| | 133 | 1.50 | 0.96, 2.36 | 0.077 |
| | 135 | 1.11 | 0.64, 1.93 | 0.716 |
| | 137 | 3.73 | 0.98, 14.22 | 0.054 |
| Fas-L | Baseline (241) | 1.00 | — | — |
| | 233 | 5.77 | 0.63, 52.9 | 0.121 |
| | 235 | 2.03 | 0.44, 9.33 | 0.365 |
| | 237 | 4.23 | 0.76, 23.67 | 0.100 |
| | 239 | 1.69 | 1.23, 2.33 | 0.001‡ |
| | 243 | 0.90 | 0.59, 1.38 | 0.628 |
| | 245 | 0.44 | 0.10, 1.92 | 0.272 |
| CTLA-4 | Baseline (88) | 1.00 | — | — |
| | 94 | 0.71 | 0.11, 4.67 | 0.724 |
| | 102 | 3.18 | 0.61, 16.65 | 0.170 |
| | 104 | 1.12 | 0.62, 2.02 | 0.704 |
| | 106 | 0.72 | 0.50, 1.03 | 0.070 |
| | 108 | 1.85 | 0.88, 3.90 | 0.106 |
| | 110 | 3.06 | 0.97, 9.67 | 0.056 |
| | 112 | 1.28 | 0.20, 8.31 | 0.793 |
| | 114 | 5.57 | 0.60, 51.41 | 0.129 |
| | 118 | 1.19 | 0.23, 6.16 | 0.829 |
| | 122 | 2.66 | 0.24, 29.93 | 0.428 |

TABLE 5-continued

Association between SLE and specific alleles
of bcl-2, IL-10, and Fas-L, but not CTLA-4*

| Allele | OR† | 95% CI | |
|---|---|---|---|
| 124 | 1.32 | 0.38, 4.64 | 0.662 |
| 126 | 0.61 | 0.15, 2.51 | 0.492 |
| 128 | 1.18 | 0.16, 8.62 | 0.865 |

*Each allele of the IL-10, bcl-2, Fas-L and CLTA-4 loci was compared with a baseline allele of the corresponding locus. The most common allele in the control group for a given locus was chosen as the baseline allele. Shown are the odds ratios (OR) and the 95% confidence intervals (CI) of the association between systemic lupus erythematosus (SLE) and various alleles of the 4 loci compared with baseline.
†Wald $X^2$ test, testing $H_0$: OR = 1 for each allele, compared with baseline.
‡Significant at the 0.05 level after Bonferroni adjustment, to control the Type I error rate across multiple comparisons within a locus.

TABLE 6

Tests for interaction between loci*

| Locus 1 | Locus 2 | $X^2$ | P |
|---|---|---|---|
| IL-10 (127) | Fas-L (239) | 0.8† | 0.37 |
| IL-10 (127) | bcl-2 (193) | 8.11 | 0.004 |
| Fas-L (239) | bcl-2 (193) | NA‡ | — |

*The likelihood ratio $X^2$ test was used to determine whether each interaction significantly improved the fit compared with a model including only the component main effects of the 2 loci. There were not enough cases and controls carrying high-risk alleles at both bcl-2 and Fas-L to permit estimation of an interaction between these loci.
†Likelihood ratio $X^2$ for $H_0$: no interaction effect.
‡Not applicable: insufficient data to calculate likelihood ratio $X^2$.

Taken together, the data presented show a novel association between 3 genes involved in apoptosis, bcl-2, Fas-L, and IL-10. CTLA-4 did not exhibit an association with SLE. Furthermore, surprisingly, we have demonstrated a synergistic effect between the susceptibility allele 193 of the bcl-2 gene and the susceptibility allele 127 of the IL-10 gene in determining disease susceptibility.

TABLE 7

Synergistic effect of IL-10 and bcl-2 lock on SLE*

| | | Sample Size | | | |
|---|---|---|---|---|---|
| IL10 | bcl-2 | Controls | Cases | OR | 95% CI |
| x/x | y/y | 161 | 87 | 1.00 | — |
| 127/x, 127/127 | y/y | 31 | 27 | 1.61 | 0.90, 2.87 |
| x/x | 193/y | 18 | 20 | 2.06 | 1.03, 4.09 |
| 127/x, 127/127 | 193/y | 1 | 22 | 40.71 | 5.40, 307.2 |

*The odds ratios (ORs) shown are based on the parametric estimates in a logistic model. x indicates any allele other than 127 for IL-10; y indicates any allele other than 193 for bcl-2. SLE = systemic lupus erythematosus; 95% CI = 95% confidence interval.

In a case-control study investigating associations between a disease and one or more genes, there is the potential for bias in odds ratio estimates due to ethnic confounding, commonly called population stratification. Depending on the relationship between an ethnic confounder and the disease, the gene-disease odds ratio may either be positively or negatively biased. In practice, it is impossible to determine the direction of bias unless the confounding variable(s) can be directly measured and controlled for in the analysis. In this study, we minimized the problem by obtaining both cases and controls from the same ethnic group (Mexican Americans), with the additional requirement that the maternal and paternal grandparents of both cases and controls must have been born in Mexico.

The markers we used are short tandem repeat sequences located in the noncoding regions of their respective genes. We relied on principles of linkage disequilibrium in our tests of association and in the corresponding inference that the genes as a whole might play a role in the SLE disease process. Linkage disequilibrium is valid over small genetic distances (within 1 or 2 centimorgans), which obviously covers the intrageneic ranges of the genes in the study. In the future it is likely to be found that such sequences are functionally relevant to the expression and biologic properties of these gene products.

Whereas the IL-10 and the bcl-2 genes are both located on chromosome 1 in the mouse, in the human, they reside on separate chromosomes; IL-10 is on chromosome 1q31-q32, and the bcl-2 gene is on 18q21. Therefore, these genes are not in linkage disequilibrium and the appearance of IL-10 susceptibility alleles together with bcl-2 susceptibility alleles in SLE patients represents a true synergism.

EXAMPLE 6

Application of the Test to Other Ethnic Groups

The identification of disease-associated alleles for SLE in a Mexican American population is a clear indication that they will be present in other ethnic groups. However, the specific disease-associated allele may differ. For example the Caucasian and Mexican American population share 80–90% similar genetic background. It is likely that they will share disease-associated alleles. However, other ethnic groups may have different disease-associated alleles. Therefore, the test for genetic predisposition in other ethnic groups would be as follows:

A test group and a control group is identified. A PCR is performed on each of the apoptotic genes, bcl-1, IL-10, Fas-L, and CTLA-4 using the primers as in Example 2. The size of the PCR products is determined. Patients with SLE are compared to a control group to determine the disease-associated allele (by size or sequence). The test involves identifying the presence of that allele for at least two and up to four of the apoptotic genes.

Turner et al (Eur J Immunogenet 1997:24:1–8) identified a single basepair polymorphism at −1082 in the promoter region of the human IL-10 gene which constitutes a G-to-A substitution. Production of IL-10 following concanavalin A stimulation of peripheral blood lymphocytes from individuals carrying a G at position −1082 was significantly increased compared with those with an A at that position. The IL-10 dinucleotide marker used in the present study is located within 50 basepairs of the −1082 G/A polymorphism. It is likely, therefore, that there is linkage disequilibrium between the 2 polymorphisms. Without wishing to be bound by the hypothesis, it is likely that these polymorphisms directly affect transcription factor binding and rates of transcription.

EXAMPLE 7

Application to Other Autoimmune Diseases

Our data on the interaction between bcl-2 and IL-10 underscore the importance of genes that regulate apoptosis in autoimmunity. Transgenic mice that over-express bcl-2 in B lymphocytes exhibit polyclonal expansion and extended survival in vitro. After a few months, these mice develop autoimmune syndromes resembling SLE, including the appearance of antihistone and anti-Sm autoantibodies and immune complex-mediated nephritis. Recent studies in SLE patients suggest that bcl-2 expression is elevated in both B and T lymphocytes.

Therefore, it can be easily envisioned that a comparable test for other autoimmune diseases would follow easily from the above test for SLE. Different autoimmune diseases share susceptibility regions on the chromosomes. Therefore, a test for particularly Thyroid autoimmunity syndromes such as Graves disease, insulin dependent diabetes mellitis, inflammatory bowel disease, rheumatoid arthritis and other arthritidies would be apparent from the SLE test.

The test for other autoimmune diseases would be as follows: A test group and a control group is identified. A PCR is performed on each of the apoptotic genes, bcl-1, IL-10, Fas-L, and CTLA-4 using the primers as in Example 2. The size of the PCR products is determined. Patients with SLE are compared to a control group to determine the disease-associated allele (by size or sequence). The test involves identifying the presence of that allele for at least two and up to four of the apoptotic genes. Alternatively different primers could be used for the PCR.

In addition, the test for apoptotic susceptibility loci could be administered with other tests for autoimmunities to get a more definitive diagnosis or test for predisposition. The disease-associated allele would again have to be identified.

Regarding IL-10, elevated levels of this cytokine are found in SLE patients. In addition, IL-10 prevents the spontaneous death of human splenic B cells in vitro, an effect that is abolished by neutralizing anti-IL-10 antibody. IL-10 inhibits apoptotic cell death in human T cells starved of IL-2 and promotes the in vitro survival of T lymphocytes from patients with infectious mononucleosis that, otherwise, are destined to die by apoptosis. These findings are of importance because the continuous administration of IL-10 to lupus-prone (NZB×NZW)F$_t$ mice accelerated, and neutralizing anti-IL-10 antibody delayed the onset of autoimmunity. Furthermore, the protective effect of IL-10 against B cell death is associated with an increased expression of bcl-2. Our data on the synergistic effect of IL-10 and bcl-2 in human SLE provides a genetic basis for these observations. The date are consistent with the notion that the maintenance of a high-level anti-apoptotic state in lymphocytes contributes to the pathogenesis of SLE by sustaining the rate of production of autoreactive antibodies.

The distal portion of human chromosome 1 (q41-q42) has been recently shown to contain an SLE susceptibility gene. Although the IL-10 gene resides on the distal portion of human chromosome 1, its exact location is proximal to the q41 region and, therefore, IL-10, but not the q41-q42 region, is closer to the chromosomal interval previously mapped in lupus-prone mice. The recent identification of the q41-q42 susceptibility region on chromosome 1, together with our data, identifies a presently unknown, SLE susceptibility gene.

Conclusion

In summary, given the anti-apoptotic nature of bcl-2 and under certain conditions, IL-10, our data further support the notion that inappropriate elimination of autoreactive lymphocytes is an important event in the development of SLE and other autoimmunities. We demonstrate here for the first time that a specific combination of 2 distinct genes that regulate apoptosis identifies a human predisposition to an autoimmune disease. In addition we provide a method for determining genetic predisposition to systemic lupus erythrematosus and other autoimmune diseases by genotyping Il-10, bcl-2, Fas ligand and other apoptotic genes.

What is claimed is:

1. A method for determining predisposition to an autoimmune disease in a patient, comprising:
   a) obtaining a sample containing genetic material from said patient; and
   b) determining whether alleles associated with susceptibility to said autoimmune disease are present in both IL-10 and bcl-2 loci in said sample, wherein the presence of both said alleles indicates that said patient has a predisposition to said autoimmune disease.

2. The method of claim 1, wherein the determining step comprises amplification of said genetic material.

3. The method of claim 2, wherein the amplification makes use of a primer specific for said allele associated with susceptibility to said autoimmune disease.

4. The method of claim 1, wherein the determining step comprises hybridization with a probe specific for said allele associated with susceptibility to said autoimmune disease.

5. The method of claim 1, wherein the IL-10 gene is amplified with primers comprising the sequences of SEQ ID NO:1 and SEQ ID NO:2.

6. The method of claim 2 wherein a bcl-2 disease-specific allele is amplified with primers comprising the sequences of SEQ ID NO:3 and SEQ ID NO:4.

7. The method of claim 1 wherein the allele associated with susceptibility to said autoimmune disease is identified by its size.

8. The method of claim 1 wherein the alleles associated with susceptibility to said autoimmune disease are IL-10 (127) and bcl-2(193) and wherein presence of both alleles indicates a greater likelihood of predisposition to said autoimmune disease than presence of either allele alone.

9. The method of claim 1 wherein the autoimmune disease is selected from the group consisting of; systemic lupus erythematosis, thyroid autoimmunity syndromes, insulin dependent diabetes mellitis, inflammatory bowel disease, rheumatoid arthritis and other arthritidies.

10. The method of claim 9 wherein the disease is systemic lupus erythematosis.

* * * * *

SEQUENCE LISTING

<160> NUMBER OF SEQ ID NOS: 8

<210> SEQ ID NO 1
<211> LENGTH: 20
<212> TYPE: DNA
<213> ORGANISM: Artificial Sequence
<220> FEATURE:
<223> OTHER INFORMATION: PCR primer to IL-10 microsatellites.

<400> SEQUENCE: 1
gcaacactcc tcgtcgcaac                                               20

<210> SEQ ID NO 2
<211> LENGTH: 22
<212> TYPE: DNA
<213> ORGANISM: Artificial Sequence
<220> FEATURE:
<223> OTHER INFORMATION: PCR primer to IL-10 microsatellite

<400> SEQUENCE: 2
cctcccaaag aagccttagt ag                                            22

<210> SEQ ID NO 3
<211> LENGTH: 25
<212> TYPE: DNA
<213> ORGANISM: Artificial Sequence
<220> FEATURE:

```
<223> OTHER INFORMATION: PCR primer to bcl-2 microsatellite.

<400> SEQUENCE: 3
cgtgtacaca ctctcataca cggct                                              25

<210> SEQ ID NO 4
<211> LENGTH: 20
<212> TYPE: DNA
<213> ORGANISM: Artificial Sequence
<220> FEATURE:
<223> OTHER INFORMATION: PCR primer to bcl-2 microsatellite.

<400> SEQUENCE: 4
gggagggtgc gccatgaaaa                                                    20

<210> SEQ ID NO 5
<211> LENGTH: 25
<212> TYPE: DNA
<213> ORGANISM: Artificial Sequence
<220> FEATURE:
<223> OTHER INFORMATION: PCR primer to Fas-L microsatellite.

<400> SEQUENCE: 5
cacttctaaa tgcatatcct gagcc                                              25

<210> SEQ ID NO 6
<211> LENGTH: 28
<212> TYPE: DNA
<213> ORGANISM: Artificial Sequence
<220> FEATURE:
<223> OTHER INFORMATION: PCR primer to Fas-L microsatellite.

<400> SEQUENCE: 6
tgtcaggaag cattcaaaat cttgacca                                           28

<210> SEQ ID NO 7
<211> LENGTH: 20
<212> TYPE: DNA
<213> ORGANISM: Artificial Sequence
<220> FEATURE:
<223> OTHER INFORMATION: PCR primer to CTLA-4 microsatellite.
<300> PUBLICATION INFORMATION:
<301> AUTHORS: Polymeropoulos, et al.
<303> JOURNAL: Nucleic Acids Research
<304> VOLUME: 19
<305> ISSUE: 1991
<306> PAGES: 4018

<400> SEQUENCE: 7
gccagtgatg ctaaaggttg                                                    20

<210> SEQ ID NO 8
<211> LENGTH: 20
<212> TYPE: DNA
<213> ORGANISM: Artificial Sequence
<220> FEATURE:
<223> OTHER INFORMATION: PCR primer to CTLA-4 microsatellite.
<300> PUBLICATION INFORMATION:
<301> AUTHORS: Polymeropoules, et al.
<303> JOURNAL: Nucleic Acids Research
<304> VOLUME: 19
<305> ISSUE: 1991
<306> PAGES: 4018

<400> SEQUENCE: 8
aacatacgtg gctctatgca                                                    20
```